(12) United States Patent
Maresca, Jr. et al.

(10) Patent No.: US 9,004,753 B1
(45) Date of Patent: Apr. 14, 2015

(54) INFRARED DETECTION OF DEFECTS IN WIND TURBINE BLADES

(75) Inventors: Joseph W. Maresca, Jr., Sunnyvale, CA (US); Wesley L. Bratton, Richland, WA (US); Wilhelmina C. Leuschen, Kennewick, WA (US); David A. Rohrig, Richland, WA (US)

(73) Assignee: Kurion, Inc., Richland, WA (US)

( * ) Notice: Subject to any disclaimer, the term of this patent is extended or adjusted under 35 U.S.C. 154(b) by 0 days.

(21) Appl. No.: 13/200,914

(22) Filed: Oct. 3, 2011

Related U.S. Application Data

(60) Provisional application No. 61/404,356, filed on Oct. 1, 2010.

(51) Int. Cl.
*G01N 25/00* (2006.01)
*G01B 5/28* (2006.01)
*G01J 5/00* (2006.01)

(52) U.S. Cl.
CPC ...................................... *G01J 5/0088* (2013.01)

(58) Field of Classification Search
USPC ................ 374/45; 73/112.01, 114.01, 114.09
See application file for complete search history.

(56) References Cited

U.S. PATENT DOCUMENTS

| | | | |
|---|---|---|---|
| 6,356,346 B1* | 3/2002 | Hagen et al. | 356/237.1 |
| 6,570,175 B2* | 5/2003 | Bales et al. | 250/559.4 |
| 6,721,461 B1* | 4/2004 | Nichani | 382/270 |
| 7,136,518 B2* | 11/2006 | Griffin et al. | 382/133 |
| 2005/0063450 A1* | 3/2005 | Willsch et al. | 374/57 |
| 2007/0288177 A1* | 12/2007 | Rothenfusser et al. | 702/40 |
| 2008/0022775 A1* | 1/2008 | Sathish et al. | 73/606 |
| 2009/0201971 A1* | 8/2009 | Goldammer et al. | 374/45 |
| 2009/0245321 A1* | 10/2009 | Ringermacher et al. | 374/5 |
| 2009/0255332 A1* | 10/2009 | Bunker et al. | 73/204.11 |
| 2011/0235672 A1* | 9/2011 | Shepard et al. | 374/45 |

* cited by examiner

*Primary Examiner* — Laura Martin
*Assistant Examiner* — Nasir U Ahmed
(74) *Attorney, Agent, or Firm* — K&L Gates LLP

(57) ABSTRACT

A method and an apparatus for detecting defects in the composite materials of a wind turbine blade or similar type of structure using an infrared (IR) camera. The temperature of the wind turbine blade is changed in such a way as to produce IR intensity changes in the region of the defect that can be visually detected or detected using a computer and signal processing algorithms. The same approach will work on other composite structures such as those found on aircraft.

44 Claims, 16 Drawing Sheets

INFRARED DETECTION OF DEFECTS IN WIND TURBINE BLADES

RELATED APPLICATION

This application claims the benefit of U.S. Provisional Patent Application Ser. No. 61/404,356 filed Oct. 1, 2010.

BACKGROUND

1. Field of the Invention

A method and an apparatus for detecting defects in the composite materials of a wind turbine blade or similar type of structure using an infrared (IR) camera, where the defects may be separation of the layers between different composite materials, waves or wrinkles in the composite layers, separation of the layers within the composite material, layers in the composite where the resin did not fully wet the cloth layer, or liquid such as water that may have infiltrated such layer defects. The temperature of the wind turbine blade relative to the ambient temperature is changed in such a way as to produce IR intensity changes in the region of the defect that can be visually detected, or detected using a computer and a signal processing algorithm. The same approach will work on other composite structures such as those found on aircraft.

2. Brief Description of Prior Art

The method and apparatus of the present invention is motivated by the need for a low-cost, reliable, and fast method of identifying defects in the composite materials of a wind turbine blade, or other similar type of composite structure, where the defects may be separation of the layers between different composite materials, waves or wrinkles in the composite layers, separation of the layers within the composite material, layers in the composite where the resin did not fully wet the cloth layer, or liquid such as water that may have infiltrated such layer defects. While IR methods have been used to detect defects such as these in wind turbine blades, these methods have generally been limited to defects near the surface. In addition, for some of the methods, the time required to complete a measurement has been too long to be operationally attractive. The composites comprising these blades might be 20 to 40 mm thick, or more.

FIG. 1a shows a typical cross-section of a wind turbine blade 10, and FIG. 1b illustrates two types of defects, delamination 38 and lack of glue 40, that could be present in a wind blade 30. FIG. 1a shows the leading edge 12 of the wind blade, the upper shell 14, the lower shell 18, the trailing edge 16, the main spar 20, and the inside of the blade 22. In FIG. 1b, the wind blade shell 30 is comprised of a glass fiber reinforced plastic (GFRP) skin layer 32, a glue layer 34, and a thicker GFRP wall 36. Defects from lack of glue 40 and delamination 38 are illustrated. The preferred embodiment of the present invention requires fluid access to the inside of the blade, and will work on any structure that allows a fluid to be transported to all sections of the inside of the composite. The alternative embodiment only requires access to one side (i.e., the outer side) of the composite.

FIG. 2 shows a typical cross-section of a wind turbine blade 50 based on the blade 10, 30 shown in FIGS. 1a and 1b and illustrates potential locations of defects that we evaluated the performance of the present invention. It was assumed that the composite was 20-mm-thick 58 and was comprised of three layers 52, 54, 56 with the possibility of defects 60, 62, 64, 66, 68 occurring in each layer 60, 66, 68 and between the layers 62, 64. The composite is comprised of three sections: (1) a 3-mm GFRP layer (glass fiber reinforced plastic) on the top of the blade 52, (2) a 12-mm GFRP layer on the bottom of the blade 56, and (3) a 5-mm glue-form layer separating these two layers 54.

Previously, we have developed an IR inspection method for aircraft honeycomb structures using a conductive heating method that can be used to detect defects in wind blade composites. This method entailed heating the surface of the composite conductively with a silicon heating mat for a short period of time (10 s) and then analyzing the IR image for defect obtained using an uncooled IR camera. Each measurement had a coverage area of approximately 2 ft$^2$. This method, however, will have difficulties in detecting the presence of defects 68 in the deepest portion of the composite structure, particularly in the deeper portions of the third layer 68. Since the method takes 30 s or more to complete a measurement, with each measurement covering only several square feet of surface area, it could take the better part of a day to completely inspect a wind turbine blade.

FIG. 3 illustrates the temperature of the defect signal 70 occurring from a defect 64 found between the glue-form layer 54 and the bottom GFRP layer 56 using the conductive method of inspection. In this case, the composite structure is heated conductively for about 10 s to increase the temperature of the surface of the composite and then removed. Only small temperature changes are required (e.g., typically 3° C.) to produce a detectable IR signal 70 that is significantly greater than the background IR intensities. For this computation, we assumed a 1-in. by 2-in. delamination-type defect and a 6° C. temperature change. The model result, which has been validated by actual IR measurements, clearly indicates that the conductive method of heating will easily detect such a defect. The model results also suggest that the method will have problems detecting defects closer to the inside surface of the composite deep within the third layer of the composite.

SUMMARY OF THE INVENTION

It is the object of this invention to provide a method and an apparatus for detecting defects within and between composites materials comprising a wind turbine blade or similar type of structure.

It is another object of this invention to provide a method and an apparatus for changing the temperature of the wind turbine blade or similar type of structure in such a way as to produce a detectable temperature change at the surface of the composite due to the defects.

It is another object of this invention to provide a method and an apparatus for changing the temperature of the wind turbine blade or similar type of structure in such a way as to produce a temperature change at the surface of the composite due to the defects that is detectable with an uncooled IR camera.

It is still another object of this invention to provide a method for automatically determining whether or not a defect is present in the composite materials of a wind turbine blade or similar type of structure through the application of signal processing algorithms implemented on a computer.

The invention described in FIG. 4 provides a method and an apparatus for reliably and quickly detecting defects throughout the entire thickness of the composite materials comprising a wind turbine blade or similar type of structure using an IR camera. The preferred embodiment of the present invention requires a means of cooling air 86 and blowing this cooled air 84 through the inside region of the blade to lower the temperature inside the blade below the temperature of the composite material and the outside ambient temperature. This produces identifiable temperature changes on the surface of the composite structure that can be detected with an uncooled IR camera 80. The IR intensity changes associated with the defects can be identified by visual inspection of an IR image or by computer 82 using a noise cancelled IR image. Once the IR detectable signals are produced due to the cooling method, a hand-held IR camera can be moved continuously and rapidly along the entire length of the blade to record IR images of the surface to be used in either the visual or automatic inspection process.

IN THE DRAWINGS

Figure 3:
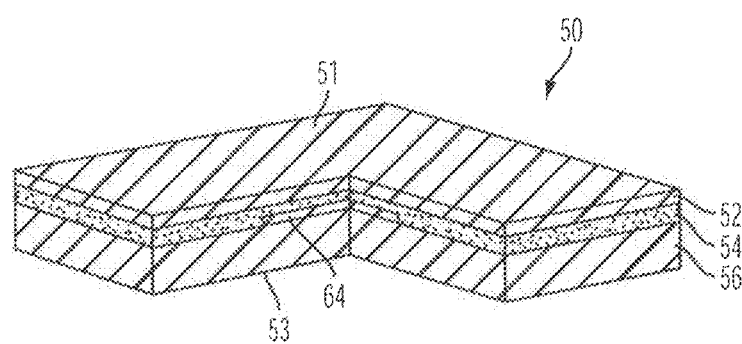
Figure 3:
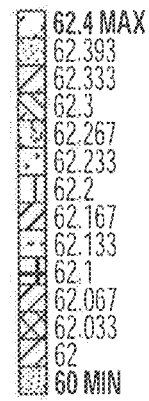
Figure 3:
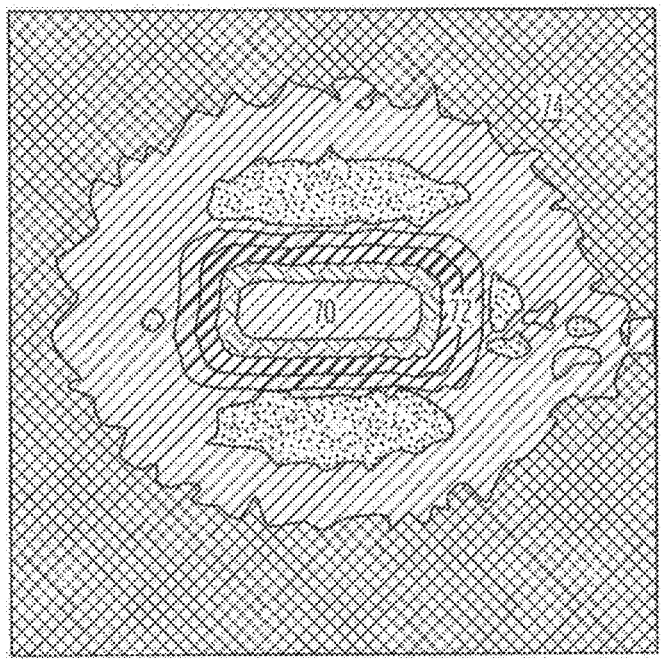

FIG. 3 illustrates a model prediction of the strength of the temperature change that occurs at the surface of the composite material after conductively heating the surface of the composite. The defect is in the wind turbine blade (or any type of composite structure) is a separation between the 5-mm glue-form layer 54 and the bottom GFRP layer at a depth of 8 mm, and (b) the expected thermal response after heating the surface 6° C. above ambient and removing the heat source.

Figure 4:
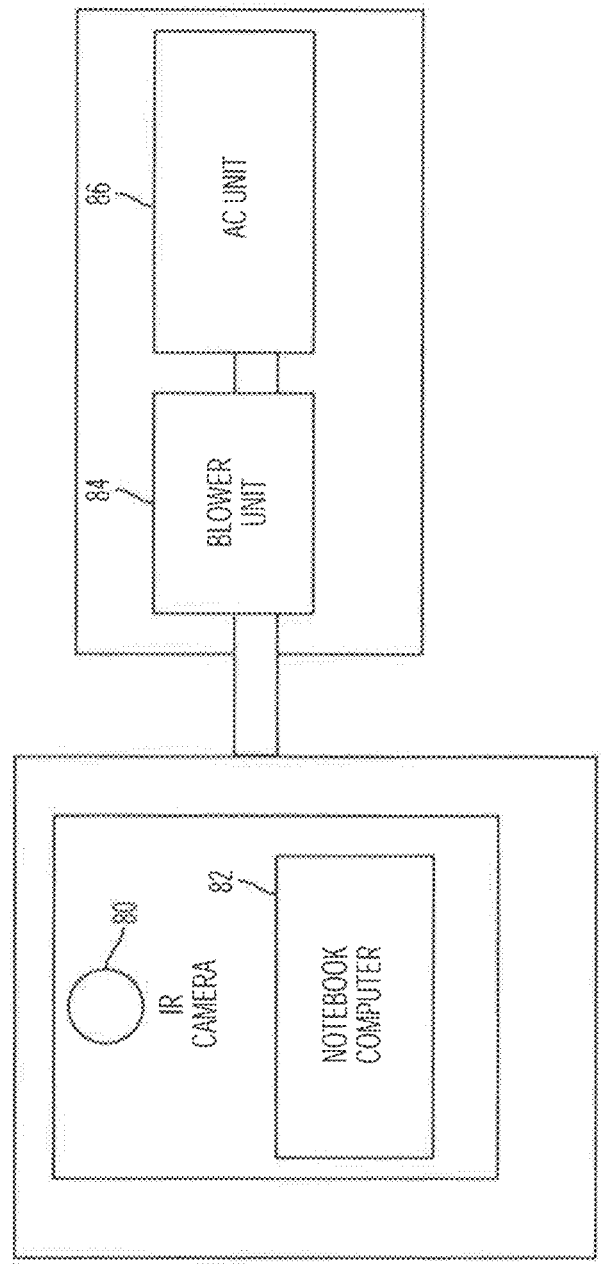

FIG. 4 illustrates the method for detecting defects in the composite materials of a wind turbine blade or similar type of structure by cooling the inside region of the blade by blowing air through the inside of the blade that is cooler than the blade.

Figure 5:
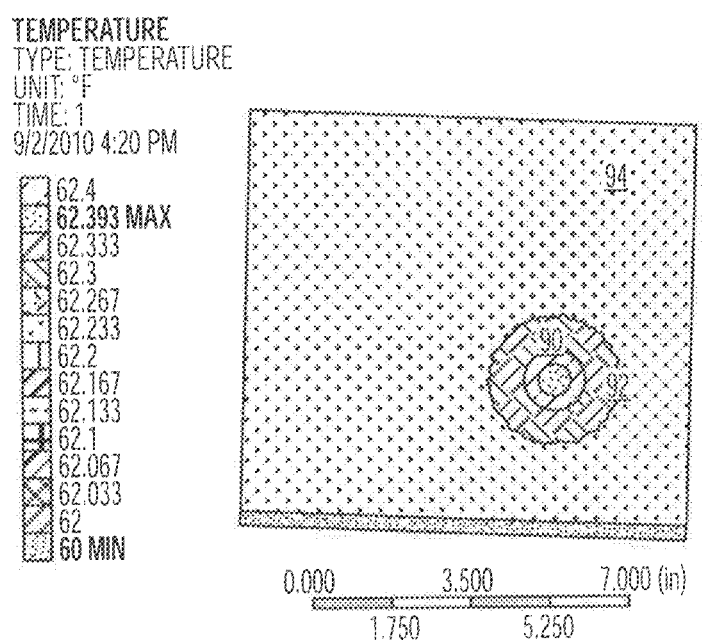

FIG. 5 illustrates a model prediction of the strength of the temperature change that occurs at the surface of the composite material after cooling the temperature of the air inside the wind turbine blade or similar type of structure. The defect is located 3-mm from the bottom of the bottom 12-mm GFRP layer at a depth of 17 mm. The surface thermal signal is very strong and easily detectable with an uncooled IR camera system.

Figure 6:
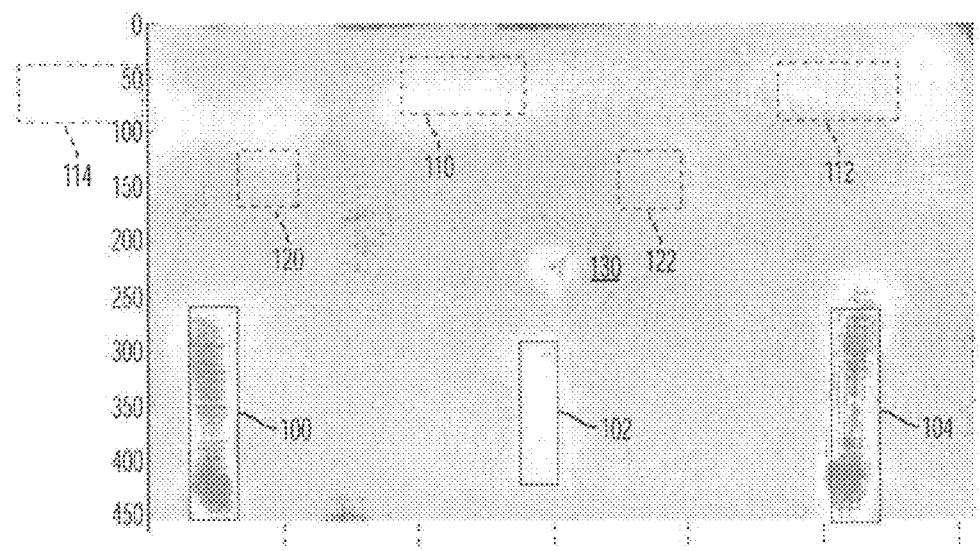

FIG. 6 illustrates the results of an IR measurement made after cooling the underside of a wind blade composite with defects inserted into the composite by Sandia National Laboratory at the mid-point and the lower one-third of the composite. This measurement simulates the cooling of the inside of a wind blade as illustrated in FIG. 5.

Figure 7:
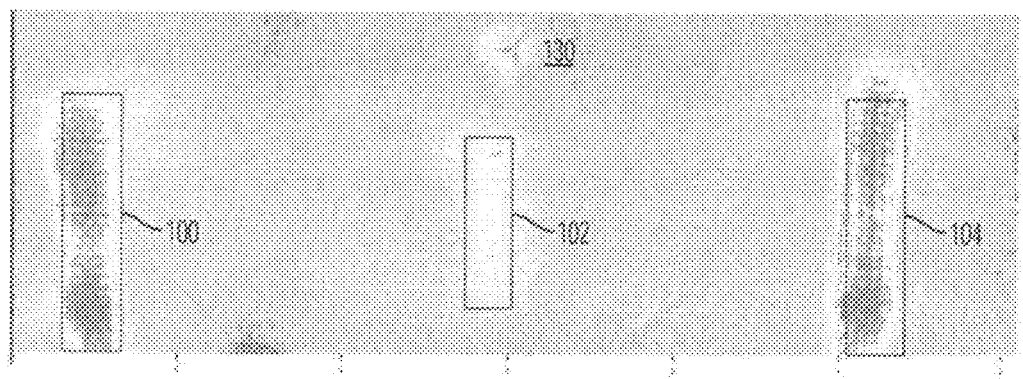

FIG. 7 illustrates the results of an IR measurement made after cooling the underside of a wind blade composite with defects inserted into the composite by Sandia National Laboratory at the mid-point and the lower one-third of the composite of the wrinkle-wave defects illustrated in FIG. 6.

Figure 8:
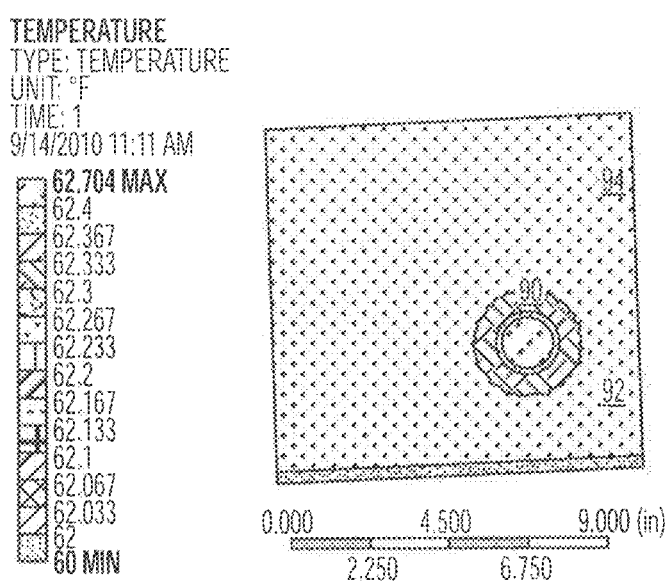

FIG. 8 illustrates a model prediction of the strength of the temperature change that occurs at the surface of the composite material after cooling the temperature of the air inside the wind turbine blade or similar type of structure. The defect is located at a depth of 8 mm from the surface between the 5-mm glue-form layer and the 12-mm GFRP bottom layer. The surface thermal signal is very strong and easily detectable with an uncooled IR camera system.

Figure 9:
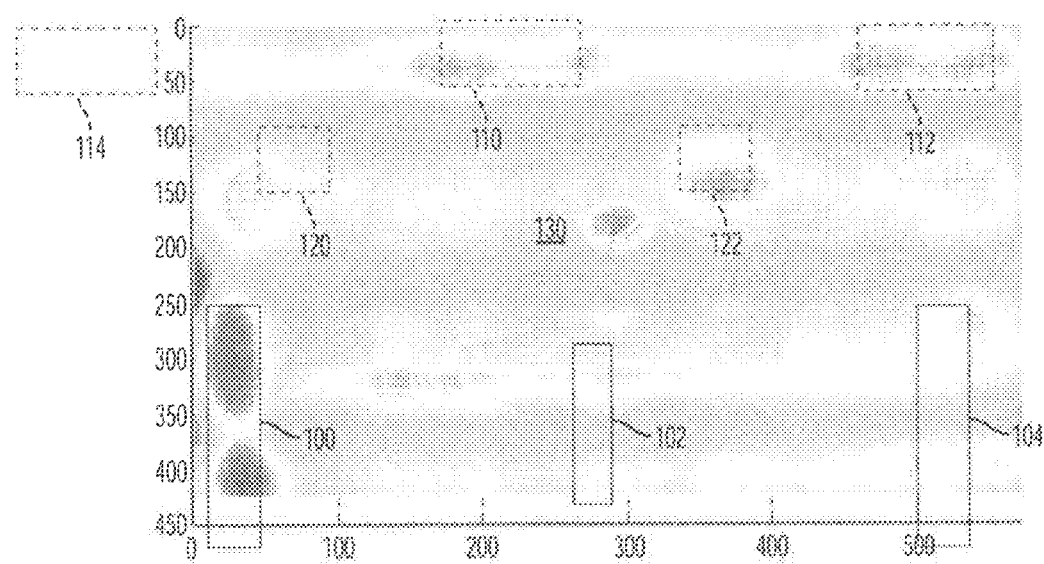

FIG. 9 illustrates the results of an IR measurement made after heating the surface of a wind blade composite conductively with defects inserted into the composite by Sandia National Laboratory at the mid-point and the upper one-third of the composite. This measurement simulates the heating of the surface a wind blade as illustrated in FIG. 3.

Figure 10:
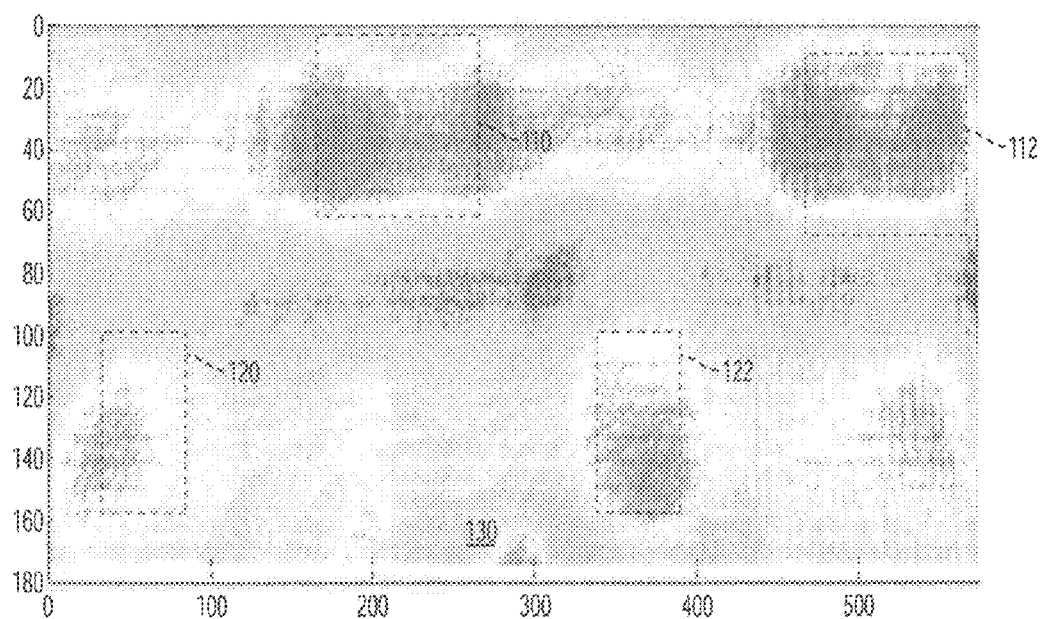

FIG. 10 illustrates the results of an IR measurement made after heating the surface of a wind blade composite conductively with defects inserted into the composite by Sandia National Laboratory at the mid-point and the upper one-third of the composite of the dry resin layer defects illustrated in FIG. 9.

Figure 11:
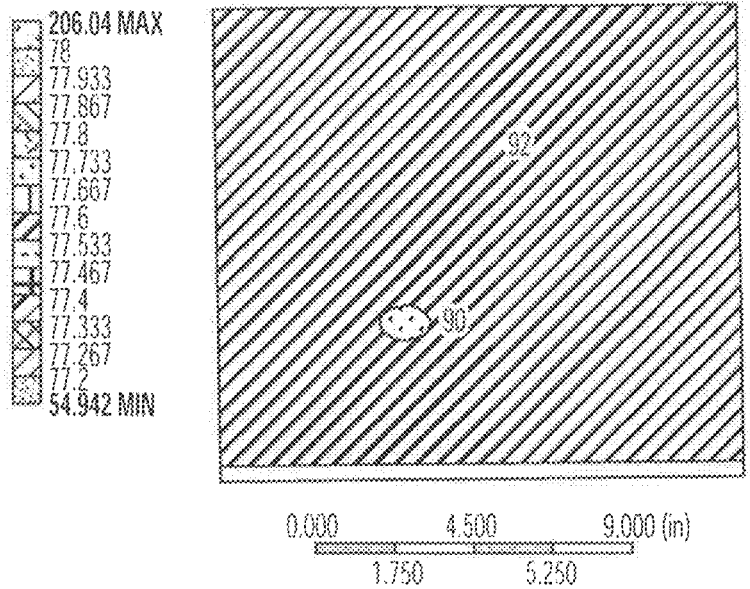

FIG. 11 illustrates a model prediction of the strength of the temperature change that occurs at the surface of the composite material after conductively heating the surface of the composite and blowing air through the inside region of the blade or similar type of structure. The defect is located 3 mm from the bottom of the 12 mm GFRP layer at a depth of 17 mm. The surface thermal signal is very strong and easily detectable with an uncooled IR camera system.

Figure 12:
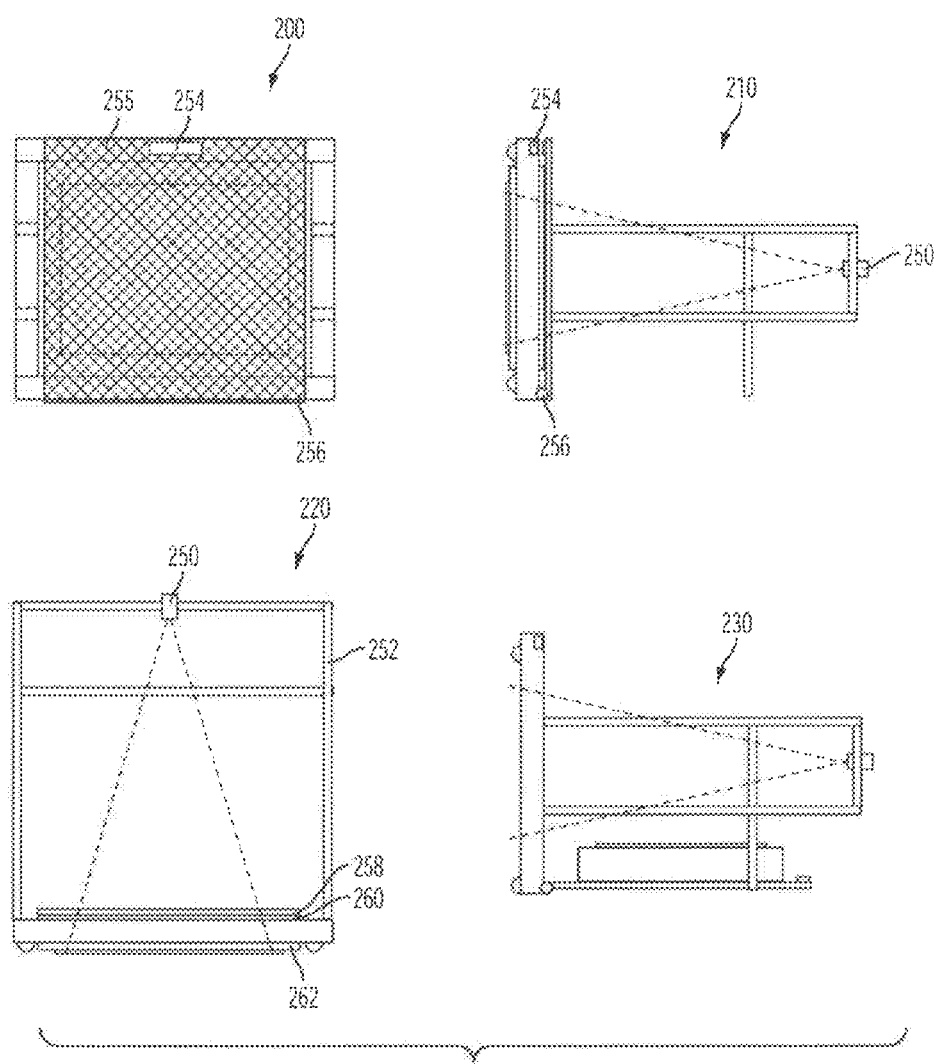

FIG. 12 illustrates the method for detecting defects in the composite materials of a wind turbine blade (or any type of composite structure) by conductively heating the surface of the blade with a heating mat.

Figure 13:
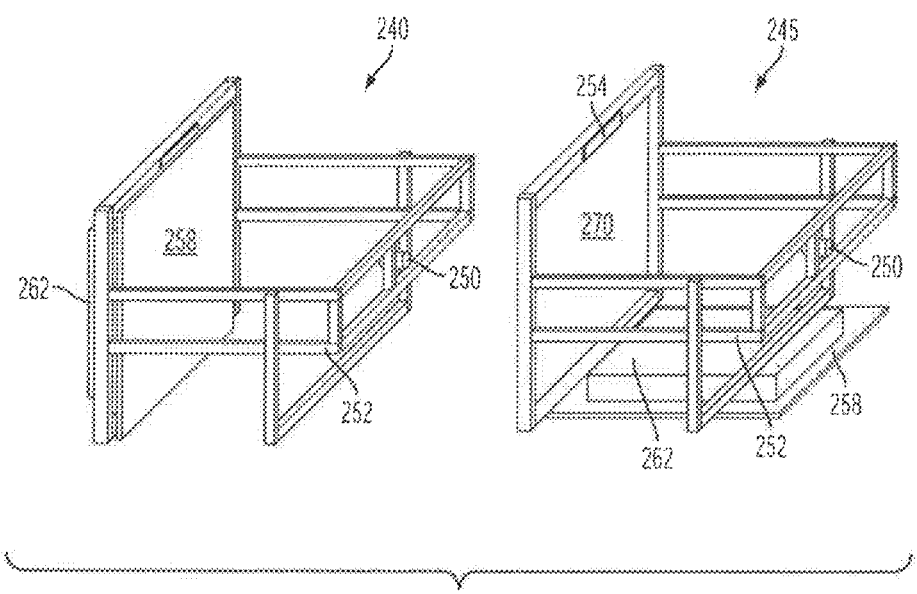

FIG. 13 shows a three-dimensional view of the conductive IR inspection system in FIG. 12.

Figure 14:
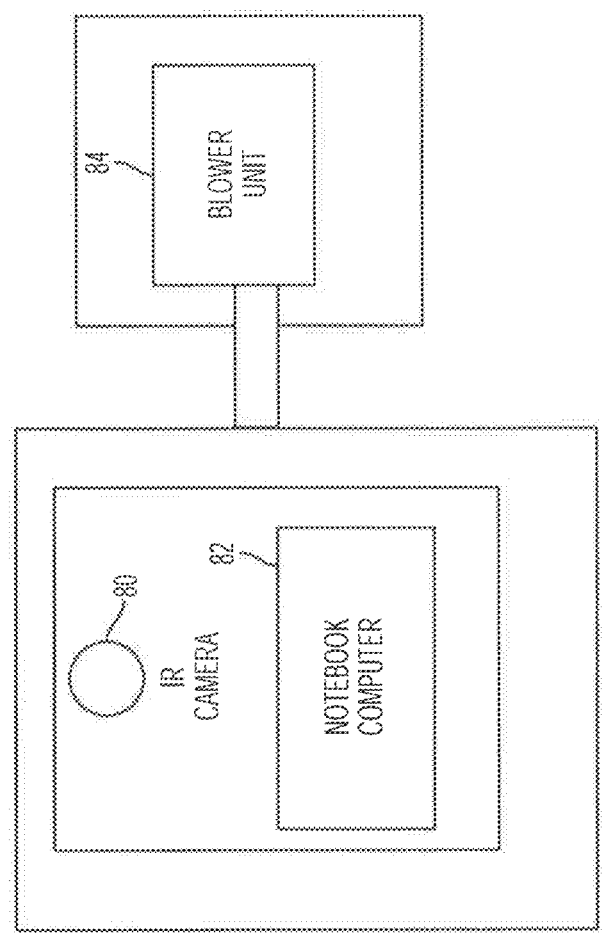

FIG. 14 illustrates the method for detecting defects in the composite materials of a wind turbine blade or similar type of structure using the conductive method illustrated in FIGS. 3, 12, and 13, but blowing air through the inside region of the blade using a blower unit.

Figure 15:
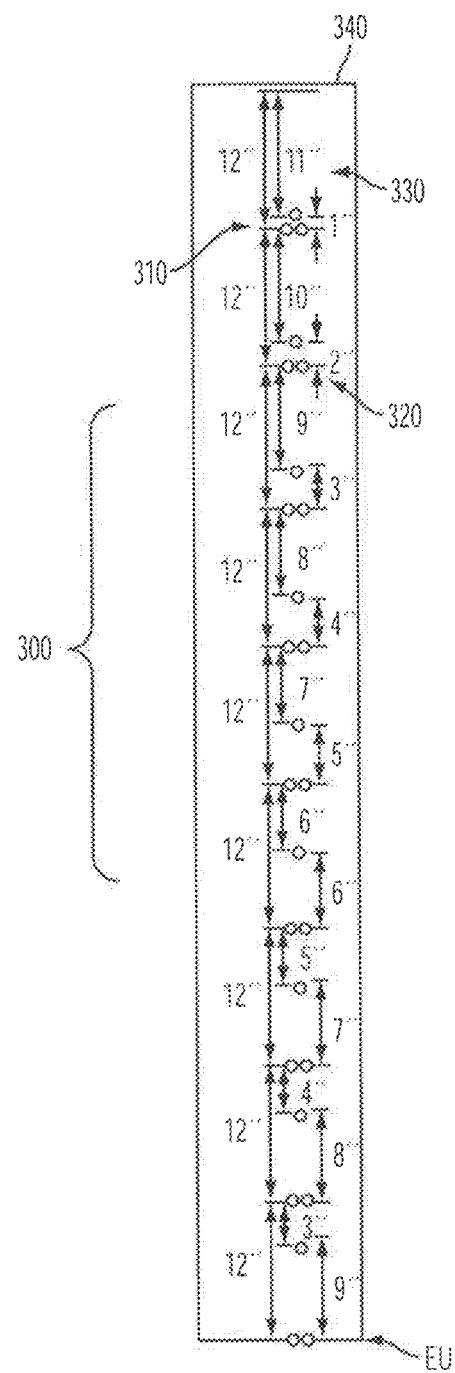

FIG. 15 illustrates a method for locating each IR image and any defects identified in such image on the wind blade composite being inspected. An IR Ruler is used to locate the IR image using standard photogrammetric methods using fiducials on the IR Ruler that are placed to allow registration of the camera and location on the wind blade. The fiducials in the preferred embodiment are electrical resistors powered by batteries. These fiducials are positioned in a pattern that is recognizable in terms of feet and inches.

DESCRIPTION OF THE PREFERRED EMBODIMENT

The method and apparatus of the preferred embodiment of the present invention is illustrated in FIG. 4. Air cooler than the temperature of the composite and the ambient air temperature is blown through the inside region of the wind turbine blade using an air conditioning unit 86 and a blower 84. The difference in the temperature of the cooler air inside the blade and the temperature of the ambient air outside the blade is sufficient to produce a change in the surface temperature of the composite associated with a defect anywhere in the composite that is strong enough to be detected with an inexpensive, uncooled IR camera 80. A hand-held IR camera 80 can be moved continuously and rapidly along the entire length of the blade to record images of the surface. The defects can be identified by visual inspection or by computer 82 using a noise cancelled IR image.

Figure 1A:
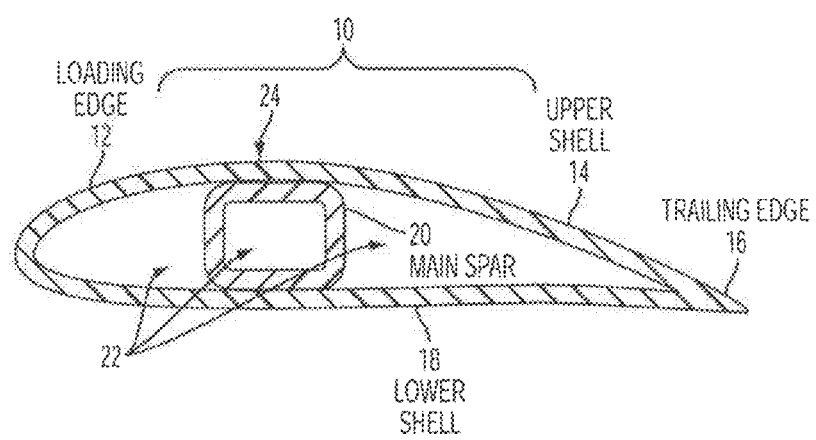
FIG. 1a illustrates a typical cross-section of a wind turbine blade.
Figure 1B:
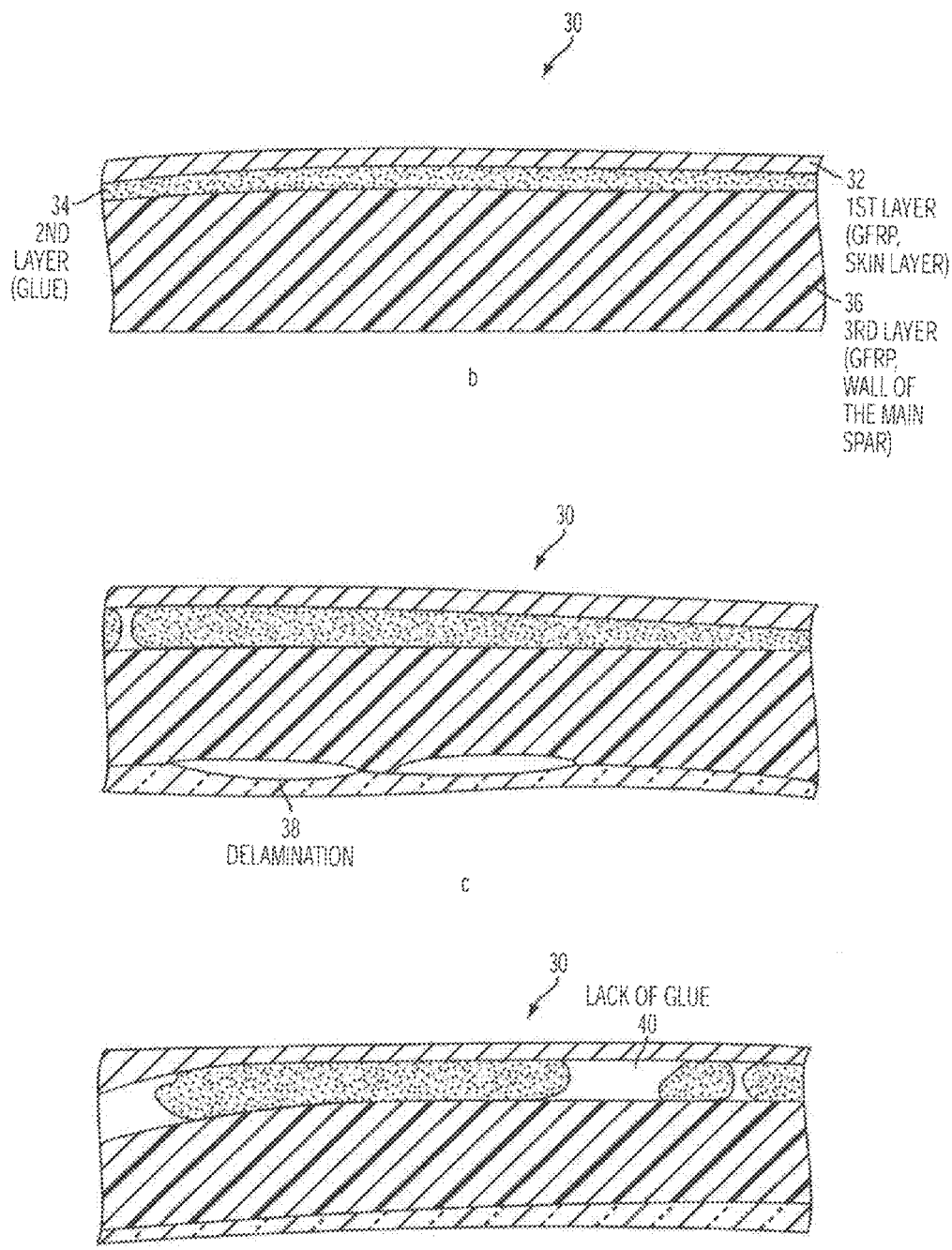
FIG. 1b illustrates defects in each of the composite layers of a typical cross-section of a wind turbine blade.
Figure 2:
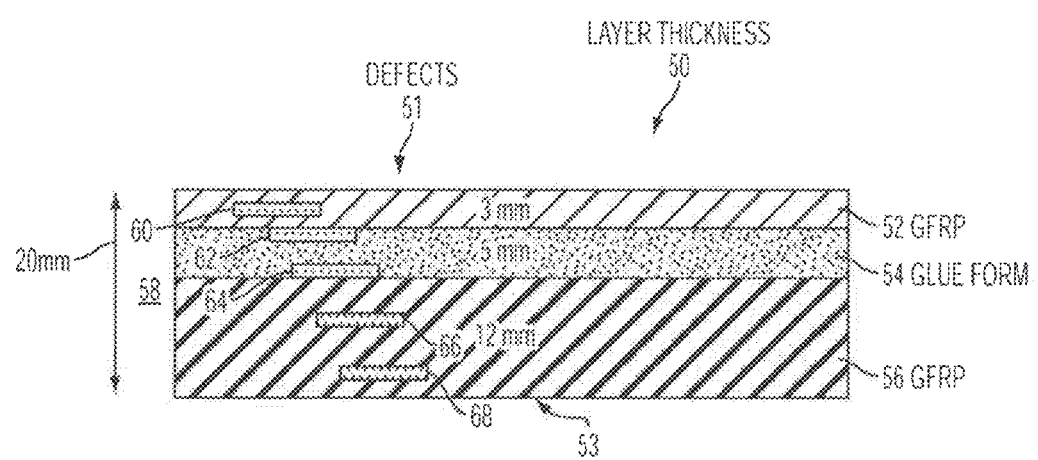
FIG. 2 illustrates a typical-cross section of a wind turbine blade with possible locations of defects in the composite materials. This cross-section and defect locations were modeled to determine the strength of the IR signal present at the surface of the blade.

FIGS. 5 and 8 illustrate the temperature change on the surface of the composite shown in FIG. 2 for a 6° C. difference in temperature between the cooler air inside the blade 22 and outside the blade 24 due to a defect located at 17 mm from the surface 68 in the bottom 12-mm GFRP layer 56 (FIG. 5) and a defect located at 8 mm from the surface 64 between the 5-mm glue-form layer 54 and the 12-mm GFRP bottom layer 56 (FIG. 8). In both cases, the temperature change at the surface 51 is large enough to be detected with an uncooled IR camera. Model computations indicate that temperature differences smaller than 3° C. will produce strong defect signals. The model results shown in FIG. 5 for the deeper defect 68 found in the lower one-third of the wind blade composite shows an IR signal 90 that is strong develops in comparison to the background IR intensities 94. The extent of the IR signal produced is also shown 92. A similar result is found in FIG. 8 for the shallower defect 64 at 8 mm. The IR intensity produced on the surface 90 is much stronger than the surrounding background 94; its extent is also illustrated 92. This result is similar to the one illustrated in FIG. 3 and obtained by only conductively heating the surface. The lower defect 68 is not detectable using only surface heating, regardless of the method of heating the surface (e.g., conductive, radiant, convective hot air).

FIG. 6 illustrates an application of the method of the present invention for detecting a defect in the bottom third of a special wind blade test sample prepared by Sandia National Laboratory that was 1.35 in. thick and consisted of 24 plies (0.056 in. per layer) of a wind blade composite material simulating a skin over spar structure. The bottom and top skin layer of the composite was each 2 plies thick. The test sample was placed on a wood frame that raised the sample about 3 in. off the floor and allowed cold air to be blown into this region with an air conditioner. The temperature of the underside of the specimen was lowered 14° F. below the 64° F. ambient temperature of the surrounding air and the test specimen. The best results occurred when the sample was heated about 10 to 30° F. above the ambient air temperature before the test began.

Two types of defects were present, but only one was located in the bottom third (at layer 16 of 24). The first type of defect 100, 102, 104, which was located in the bottom half of the display in FIG. 6, was a precured resin shape to simulate a wrinkle or wave in the composite. The approximate size and location of these defects 100, 102, 104 are denoted by the rectangular markers. The smaller wave 102 located in the middle of the figure was 4 in. long by 0.17 in. thick by 0.67 in. wide; this wave 102 was located on layer 16 of the 24 layers. The larger waves 100, 104, located to the left and right of the smaller wave 102 were 6 in. long by 0.0.33 in. thick by 1.0 in. wide. Wave 100 was located at layer 12, and wave 104 was located at layer 16. Another type of detect was located in the top half of FIG. 6. The defects 110, 112, 120, 122 were constructed of resin starved dry layers comprised of 3 layers 110, 120 and 5 layers 112, 122. The approximate size and location of these defects 1110, 112, 120, 122 are denoted by the rectangular markers. The upper and larger dry resin layers 110, 112 were 1.5 in. by 3.0 in., and the smaller and lower dry resin layers 120, 122 were 1.5 in. by 1.5 in. The dry resin areas 110, 120 were located in layers 11, 12, and 13 of the 24 layer composite. The dry resin areas 112, 112 were in layers 10, 11, 12, 13, and 14 of the 24 layer composite. The dry resin area 114 outside the IR measurement area third is shown because the edge of this defect was also detected. The defect 130 in the center of the display is a reflection of the IR camera. All three of the wave defects 100, 102, 104 are easily detected. The larger dry resin layers 110, 112 were also detected. The smaller dry resin areas are better detected in IR images taken at a different time after starting the test. Note that the wave defects located in the bottom one-third of the wind blade composite are detected. As illustrated in FIGS. 9 and 10, this is not the case when only the surface of the wind blade composite is heated. FIG. 7 better illustrates the detection of the deeper wave defects 102, 104.

FIGS. 9 and 10 illustrate the results of an IR measurement obtained when the surface of the composite was heated for 120 s with a conductive heating mat. In this case, only the wave 100 located in the middle layer (layer 12 of 24) of the wind blade composite was detected. The deeper wave defects 102, 104 were not detected. The four dry resin layer defects 110, 112, 120, 122 were detected.

To successfully detect the deeper defects using the method of heating the surface is accomplished by blowing air through the inside of the wind blade 22 during the measurement heating and IR measurements. FIG. 11 illustrates the model simulation for a defect in the lower one-third 68 of the wind blade composite illustrated in FIG. 2 for the conditions illustrated in FIG. 5. The surface thermal signal 90 is very strong compared to the background 92 and is easily detectable with an uncooled IR camera system.

The preferred embodiment of the present invention illustrated in FIG. 4 is comprised of
- a cooling system such as an air conditioning system,
- a blower system to transport the cool air created by the cooling system through the inside of the wind turbine blade,
- an IR camera system,
- a special software processor and GUI that implements the signal processing algorithms for automatic processing, and
- a notebook computer to acquire, process, display and process the IR real-time results and allow operator inspection and interpretation of the results and the video to confirm any detections.

The cooling 86 and blowing 84 system can be mounted on a small cart that can be moved from one blade to another. The IR camera is mounted on a cart that positions the camera above the blade so that the entire width of the blade can be examined in a single image as the camera is moved along the blade. An uncooled IR camera will suffice for most measurements. Once the air inside the blade is cooled, any defects in the composite will produce a detectable temperature change on the surface of the blade that can be detected with an uncooled IR camera. Since only a single image is needed to differentiate defects from the normal background, the camera can be rapidly moved along the blade to complete an inspection. The bottom of the blade can be inspected by either turning the blade over and repeating the measurement, or the camera could be mounted on a short table beneath the blade that can be moved along the blade to image the entire blade. If the blade is mounted on its side, like the one illustrated in FIG. 4, then both sides of the blade can be inspected using the same moving cart. The preferred embodiment has the advantage that the method used to produce a detectable defect signal works on the entire blade and does not require small sections of the blade to be heated or cooled. This method of producing the defect signal allows an IR camera to inspect the entire blade very quickly.

An alternative embodiment of the present invention is to use a conductive method of heating as illustrated in FIGS. 12 and 13 is comprised of
- An IR camera
- A heater and an a mechanical apparatus for applying heat over a specified area of the vertical stabilizer
- Software to collect and process IR video images of the areas being inspected with a notebook computer
- A special software processor and GUI that implements the signal processing algorithms for automatic processing
- A notebook computer to acquire, process, display and process the IR real-time results and allow operator inspection and interpretation of the results and the video to confirm any detections Several views of the system are illustrated schematically for conductive measurements is are illustrated in FIGS. 12 and 13. The IR camera 250 and the heater 262 are both incorporated as part of the frame. The heater is mounted on a foam backing 260 that is mounted on a rigid backing 258. The inside dimensions of the frame are 21.25 in. wide by 16.25 in.

high and allow a heating mat (21.0 in. by 16.0 in.) to heat the entire IR image area (20.0 by 15.0 in.). These dimensions are only presented to illustrate one example of the size of the system. It can be larger or smaller. For inspection of the wind blade composite, the frame will be held perpendicular to the composite. There are two basic configurations of frame and heater 210 or 220 during an inspection measurement: during heating of the composite 210, 200 and during IR measurement of the composite surface 230, 220. As illustrated in FIG. 13, when heat is applied to the composite 240, the heating mat is locked in place at the end of the frame and parallel to the composite so that the operator can position it and apply enough pressure to it so that the mat presses firmly to the composite surface and heats all regions of the composite beneath it. When IR measurements are made, the heating mat is located outside the view of the IR camera resting on the bottom of the frame and perpendicular to the composite.

The heater subassembly, which can swing 90 degrees on the hinge 256, will be locked to the frame by an electromagnetic latch 254, 255. The heating subassembly (comprised of 258, 260, 262) is located on a hinge 256 that runs the full extent of one side of the frame 252. The silicone heating mat 262 is mounted on a foam backing 260, and the foam is mounted to the sturdy, lightweight, flat panel 258. A steel bar 255 will run along the top extent of the board to allow one magnet to be used and to have enough weight that when the electromagnet is turn off, the heater subassembly will drop 90 degrees to the horizontal and out of the IR image 270. The electromagnetic switch 254 will be mounted at the center of the heater edge. Thus, when the operator positions the frame on the vertical stabilizer, the heater subassembly is resting on the bottom of the frame. When heat is to be applied to the composite, the heater subassembly is swung 90 degrees up and locked in place by the electromagnetic lock 254, 255. Once the heater is locked in place, it can be pushed against the composite. The frame that comes in contact with the composite will be comprised of a 1- to 2-in-diameter round rubber foot. The thickness of the foam is large enough so that it extends below the rubber feet when not uncompressed. When the operator applies pressure, the foam will compress and the heating mat will conform to any small curvature in the composite. The rubber feet allow measurements to be made of curved surfaces as well as flat surfaces. There are many different types of designs for the electromagnetic locking switch.

The hinge and magnetic latch are positioned to place the heater so it extends beyond the frame. This ensures it is pressed firmly and evenly on the composite surface. The heater extends one inch around the camera field of view. The foam backing is sandwiched between the flexible heater and a rigid backing ensuring the heater conforms to the composite surface. The hinge is mounted between the foam and heater to extend the heater or of the camera's field of view when swung away from the composite surface.

FIG. 14 illustrates the method for detecting deep defects in the wind blade composites using the conductive heating method. It is comprised of a blower unit 84 to blow air though the inside of the wind blade 22, an uncooled IR camera, and a computer 82. Without blowing air or a fluid through the inside of the wind blade, only defects in the top two-thirds of the composite will be detectable.

The IR inspection measurements can be accomplished automatically and in real-time. Instead of a person reviewing the JR intensity images and attempting to determine defects from the hot or cold IR intensity spots on the image, an automatic signal processing algorithm can be used to make a decision. The basic approach is for the automated system to make decisions and then to pass any detections or regions suspected of possible damage to an operator for final disposition. There are a number of ways to automate the inspection process to achieve the highest probability of detection ($P_D$) for detecting defect, the lowest probability of a false alarm ($P_{FA}$). The automated system controls the $P_D$ and $P_{FA}$.

Two general signal processing approaches are used. The first computes the rate of change of the IR intensity (i.e., rate of change of temperature) for each pixel over time and determines whether or not a defect is present based on whether or not the rate of change is larger than some pre-determined rate. This algorithm works well when the defect cools rapidly over time immediately after the application and removal of heat.

The second, a more general approach, is based on a noise-cancellation method that computes the background field (i.e., an undamaged portion of the composite) for each pixel over the area being inspected and then subtracts this background field at each pixel from the IR intensity measured at each pixel so that any actual defect signals can be identified. The preferred method is to use a median filter. This is accomplished by computing the median value at each pixel over the section of the composite being analyzed from a region surrounding that pixel. The median value is computed for a region surrounding each pixel, where the area of the region used in the filter is preferably at least two times larger than the defect to be detected. A square or rectangular region is most frequently used, but any area can be used (e.g., circular area). This median filter works because, while the background may even be more intense than the defect signal itself, the median value is always background and does not contain any signal. The mean value, however, does contain the contribution due to the defect signal. When this processing approach is applied to a composite with no defects, the result is an IR intensity field of random white noise (i.e., normally distributed) that has a standard deviation that is a factor of 10 to 20 times smaller than the standard deviation before removing the background and a mean of approximately zero. The IR intensities of the actual image typically range from 0.2 to 1.0. The background removal or noise cancellation processing approach works, because the rate of change of the IR intensity over the section being analyzed is small compared to the rate of change of the IR intensity in the region of a defect.

There are many ways to apply the median filter to optimize the result, but the basic approach is to estimate the background with little or no contribution due to the defect signal. There are also a wide range of filters other than the median filter described herein with similar characteristics that can be used to estimate the presence of the background with the signal also present. However, the median filter is the easiest to describe and easiest to understand how the noise cancellation approach works.

A clustering algorithm is then applied to the noise cancelled IR intensity field to determine regions or clusters of pixels that have IR intensities that are stronger or weaker than the background. A cluster is defined as a specified number of adjacent pixels (i.e., pixels that touch each other to form a group or cluster) exceeding the background field by a specified threshold amount. The size, strength, and the location of each cluster is then determined. To minimize the possibility of false alarms, the algorithm requires than a specified number of pixels exceed the threshold before a detection is declared (i.e., the minimum size of the cluster to be detected is determined by the number of pixels in the cluster). Once a detection is declared, an operator is alerted to confirm the detection or perform additional analysis before deciding if the signal detected is a defect or not.

The cluster threshold is selected to insure that the probability of false alarm, $P_{FA}$, (e.g., <1%) is low and that the probability of detection, $P_D$, (e.g., >99%) is high. This can be done because the ambient background noise level after noise-cancellation is Gaussian white noise. There are two ways to set the threshold. The first is to set it based on operational experience. The second is to adaptively set the threshold using the cumulative frequency distribution of the IR intensities determined from the background obtained during a test.

If the median filter is not applied appropriately, there are a number of false alarms (i.e., false targets) that may result from the application of the median filter. This can occur at the corners of the image, or at the corners where composites and other materials are attached, or at the corners where areas of the composite are heated and not heated. These corner effects can be identified by applying the median filter several times, where the size of the median filter is increased. The size and IR intensity of a false cluster defect increases as the size of the median filter is increase. However, this is not true of defect signals, which do not increase in size or intensity.

Ideally, the region should ideally be larger than the largest defect to be detected, but small enough to allow a good estimate of the background intensity. In operation, the algorithm will be applied iteratively using different size median filters so that all sizes of defects are capture. Fortunately, the algorithm works fine, even if the defect if greater than 50% of the median filter.

Some of the defects occur more quickly and/or decay more rapidly than others. The rate of change of the IR intensity can be used to classify the type of defect.

The processing of the IR images is accomplished in four parts. First, the raw IR intensity data are compensated for the systematic noise produced by the heater using a simple median filter noise cancellation method. In this case, the mean noise level at each pixel is estimated by computing the median value in an area centered on each and every pixel in the image. This works very well providing that any defects present are no larger in size than ⅓ to ½ the size of the median filter area. (As it turns out, this approach for estimating the underlying systematic noise works even if the defect is larger than the median filter area.) To maintain robust processing, to get the best estimate of the size of any defects detected, and to mitigate false alarms, the detection and classification analysis is performed at least three times with increasingly larger median filters. As the median filter increases in size, the IR intensity of the defects approach a constant value.

Second, any grouping of pixels with IR intensities greater than the pre-selected threshold are tagged as possible defects. The number of pixels defines the smallest targeted defect. In general, we use 16 pixels, which covers an area of 0.25 in. by 0.25 in., which is about 25% of the area of the 0.5 in. by 0.5 in. defect goal. This parameter is easy to change and can be as small as 2 to 4 pixels. This grouping of pixels insure that no random spike in a pixel (e.g., a bad data point) will result in a potential defect being declared.

Third, once a list of possible defects are identified, the defects in the list are each analyzed to determine if they are real or a false alarm. The main source of a false alarm is an unusual noise fluctuation. Our previous analyses suggest that the occurrence of such events is highly unlikely unless the threshold is set too low. False alarms produced by noise are easy to mitigate. As an example, while the peak intensity and size of a defect approach a constant value as the median filter size increases, the peak intensity and size of the IR intensities produced by false alarms continue to increase in size without bound.

Fourth, once the false alarms have been rejected, then the remaining threshold exceedances are declared to be defects, and the location, size, and classification algorithms are determined from a cluster analysis. The size of the defect is determined from the number of adjacent pixels in the cluster. The location of the cluster is determined from the centroid of the cluster.

The key part of the signal processing is the noise compensation that results in the Analyzed Image using a median filter. The ambient background is computed by selecting a region in the image, which is at least 51% larger than the defects of interest and compute a running median for each pixel for the region selected centered on the region. The median background has no effects of any defects. The median background of each pixel is then subtracted from the value at each pixel to obtain the signal field. This removes the hotter or colder intensities that occur due to uneven heating either by the heater or by the orientation or the material itself.

The location of the IR image and any defects identified and located within the IR image can be located with respect to a physical location on the wind blade composite being inspected. This accomplished by using an IR ruler with fiducials in a known location so that when they are measured by the IR camera, their location along the wind blade composite will be known. The fiducials can be measured directly in the IR camera measurement for defects or rotating the camera to include the fiducials in the IR image.

FIG. 15 illustrates one possible IR ruler. The IR ruler is a strip 300 of fabric 330, preferably felt, that is placed along the leading edge of the composite that contains an array of 310, 320 fiducials that are placed in a specific pattern, which indicates a known position along the wind blade of where the camera is located. In one embodiment of the present disclosure, the strip 300 of fabric 330 that makes up the IR ruler can be a felt mat. As used in this disclosure, the felt making up the felt mat can be a non-woven textile of fibers pressed or matted together. The felt mat can be made of natural fibers such as wool, or synthetic fibers such as acrylic. The felt mat can have a range of thickness and density to allow for placement of the fiducials 320. The pattern is made up of placing 2 resistors 310 adjacent to each other every 12 in. to indicated foot markers. From the marker that is one foot from the top of the stabilizer, another marker 320 is placed 1 inch higher. Similarly, at two feet from the top of the stabilizer, the additional marker 320 is placed 2 inches higher than the foot marker. The pattern continues down the length of the vertical stabilizer. This pattern has several advantages. First, just by looking at the spacing between the foot marker and the additional marker, the approximate position along the wind blade can be ascertained. Second, with the vertical field of view of the camera being large enough, at least 3 markers will always be in the field of view. Lastly, the pattern is unique such that there is no repetition of the spacing.

Each fiducial is an 800 ohm resistor that is power by a 9V battery pack (or can be powered with an AC wall adaptor). The heat produced by the resistor is enough to make the resistor appear as a bright spot on the IR images.

Analysis similar to the detection of flaws is used to detect the fiducials in the IR image. A threshold is applied to the IR image and clusters of pixels larger than the exceedance number are located. The results of multiple runs of three varying filters are compared to eliminate detections that are not fiducials. These detections can be objects in the background if the image or reflections on the stabilizer surface.

The distance of the fiducials to the center of the image taken if the camera was pointed straight at the composite is determined by translating the oblique fiducial image to its vertical equivalent using traditional oblique image transformation techniques. The vertical equivalent information and the known pattern of the fiducials determines at which foot marker the measurement is taken. The placement of the IRRuler on the stabilizer surface gives the user the exact placement of the measurement on the composite surface. Multiple axis translations are performed to trace the measurement to its exact location on the composite surface.

There are a variety of other means for locating the IR images on the wind blade. Acoustic or ultrasonic sensors can be place on the wind turbine blade and on the inspection frame to locate the IR image and any defects found to the actual blade being inspected.

While certain representative embodiments and details have been shown for purposes of illustrating the invention, it will be apparent to those skilled in the art that various changes in the methods and apparatus disclosed herein may be made without departing from the scope of the invention which is defined in the appended claims.

What is claimed is:

1. A method for detection of composite defects in wind turbine blades including a composite using IR images of the surface of the composite comprising the steps of:
   a. while the wind turbine blade is not in use, cooling a surface of the wind turbine blade located on an inside region of the blade;
   b. collecting an IR intensity image of the surface of the blade with an IR camera, while the wind turbine blade is statutory; and
   c. detecting defects in the composite on the surface of the wind turbine blade by identifying areas of the composite that are warmer or cooler than the surrounding background, where a background of the wind turbine blade not containing any defects is determined using a median filter as applied to the IR image to determine the background of the wind turbine blade at each pixel in the image, and where false regions that may occur at the corners of an IR image due to the median filter are identified as false defects because the size of the region of the IR image of the wind turbine blade grows as the size of the median filter increases.

2. The method of claim 1, where the inside region is cooled by blowing a fluid through an inside region of the wind turbine blade.

3. The method of claim 1, where a fluid on the inside region of the blade is cooled.

4. The method of claim 3, where said fluid is a gas.

5. The method of claim 3, where said fluid is an aerosol.

6. The method of claim 3, where said fluid is air.

7. The method of claim 1, where a fluid on the inside region of the blade is cooled below the surrounding ambient air temperature.

8. The method of claim 1, where a fluid on the inside region of the blade is cooled below the temperature of the composite material.

9. The method of claim 1, where the inside region is cooled by blowing a fluid that is cooler than the surrounding ambient air temperature through the inside region.

10. The method of claim 1, where said IR camera is an uncooled camera.

11. The method of claim 1, where said IR camera is a camera cooled to a temperature below the surrounding ambient air temperature.

12. The method of claim 1, where said median filter is applied to a region around each pixel in the IR image.

13. The method of claim 12, where said region is large enough to include the defect.

14. The method of claim 13, where said region is at least twice as big as the defect.

15. The method of claim 1, where the intensity of each pixel in the background of the wind turbine blade IR image is subtracted from the IR image containing defects to produce a noise cancelled image.

16. The method of claim 15, where a threshold is applied to said noise cancelled image to detect defects from regions of the IR image of the wind turbine blade that have higher or lower intensities.

17. The method of claim 16, where said regions of the IR image of the wind turbine blade must be a specific number of pixels to identify a defect.

18. The method of claim 1, where false regions that may occur at the corners of an IR image due to the median filter are identified as false defects because the intensity of the region of the IR image of the wind turbine blade grows as the size of the median filter increases.

19. The method of claim 1, where the inside region is cooled by blowing a fluid through an inside region of the wind turbine blade, where a background of the wind turbine blade not containing any defects is determined using a median filter as applied to the IR image to determine the background of the wind turbine blade at each pixel in the image, where the intensity of each pixel in the background of the wind turbine blade IR image is subtracted from the IR image containing defects to produce a noise cancelled image, and where the intensity of each pixel in the background of the wind turbine blade IR image is subtracted from the IR image containing defects to produce a noise cancelled image.

20. The method of claim 1, further comprising the step of heating an exterior surface of the wind turbine blade before cooling the inside region of the blade.

21. The method of claim 20, where the exterior surface of the wind turbine blade is heated with a silicon heating mat.

22. The method of claim 20, where the exterior surface of the wind turbine blade is heated to at least five degrees Fahrenheit above ambient temperature.

23. The method of claim 1, where the IR camera is cooled to at least twenty degrees Fahrenheit below ambient temperature.

24. The method of claim 1, where the IR image detects cracks in the exterior surface of the wind turbine blade.

25. The method of claim 1, where the IR image detects separation of layers of the composite material within on the exterior surface of the wind turbine blade.

26. The method of claim 1, where the IR image detects water intrusion into the composite material of the wind turbine blade.

27. The method of claim 1, where the IR image detects disbonding of the composite material of the wind turbine blade.

28. A method for detection of composite defects in wind turbine blades including a composite using IR images of the surface of the composite comprising the steps of:
   a. while the wind turbine blade is not in use, cooling a surface of the wind turbine blade located on an inside region of the blade, where the inside region of the blade is cooled by blowing a fluid through an inside region of the wind turbine blade;
   b. collecting an IR intensity image of the surface of the blade with an IR camera, while the wind turbine blade is statutory; and
   c. detecting defects in the composite on the surface of the wind turbine blade by identifying areas of the composite that are warmer or cooler than the surrounding background, where the inside region is cooled by blowing a fluid through an inside region of the wind turbine blade, where a background of the wind turbine blade not containing any defects is determined using a median filter as applied to the IR image to determine the background of the wind turbine blade at each pixel in the image, and where false regions that may occur at the corners of an IR image due to the median filter are identified as false defects because the size of the region of the IR image of the wind turbine blade grows as the size of the median filter increases.

29. The method of claim 28, where false regions that may occur at the corners of an IR image due to the median filter are identified as false defects because the intensity of the region of the IR image of the wind turbine blade grows as the size of the median filter increases.

30. A method for detection of composite defects in wind turbine blades using IR images of the surface of said composite comprising the steps of:
    a. changing the temperature of the surface of the wind turbine blade conductively;
    b. collecting an IR intensity image of the surface of the said blade with an IR camera;
    c. identifying the area in the image produced by said defect that is warmer or cooler than the surrounding background, where the background of the wind turbine blade not containing any defects is determined using a median filter as applied to the IR image to determine the background of the wind turbine blade at each pixel in the image, and where false regions that may occur at the corners of an IR image due to the median filter are identified as false defects because the size of the region of the IR image of the wind turbine blade grows as the size of the median filter increases.

31. The method of claim 30, where false regions that may occur at the corners of an IR image due to the median filter are identified as false defects because the intensity of the region of the IR image of the wind turbine blade grows as the size of the median filter increases.

32. A method for detection of composite defects in wind turbine blades including a composite using IR images of the surface of the composite comprising the steps of:
    a. while the wind turbine blade is not in use, cooling a surface of the wind turbine blade located on an inside region of the blade;
    b. collecting an IR intensity image of the surface of the blade with an IR camera, while the wind turbine blade is statutory; and
    c. detecting defects in the composite on the surface of the wind turbine blade by identifying areas of the composite that are warmer or cooler than the surrounding background, and where the IR image obtained from said IR camera and any defects identified in said IR image can be located with respect to a physical location on the wind blade composite being inspected by identifying fiducials located on said wind blade in the IR image and based on the known pattern and location of these fiducials, transforming the coordinates of said IR image and said fiducials from the image to a coordinate system on said wind blade.

33. The method of claim 32, where said fiducials are electrical resistors.

34. The method of claim 33, where the electrical resistor is at least an 800 ohm resistor.

35. The method of claim 32, where said fiducials are any material with different thermal properties than the composite.

36. The method of claim 32, where the fiducials are mounted in a felt mat.

37. The method of claim 36, where said fiducials and said felt mat are attached to a more rigid but flexible membrane such as a rubber material.

38. The method of claim 32, where the fiducials are placed along the exterior surface of the wind turbine blade such that a first set of fiducials is placed substantially every twelve inches along the exterior surface of the wind turbine blade to indicate foot markers.

39. The method of claim 38, where a second set of fiducials is placed at substantially one inch increments along the exterior surface of the wind turbine blade to indicate inch markers.

40. A method for detection of composite defects in wind turbine blades including a composite using IR images of the surface of the composite comprising the steps of:
    a. while the wind turbine blade is not in use, cooling a surface of the wind turbine blade located on an inside region of the blade;
    b. collecting an IR intensity image of the surface of the blade with an IR camera, while the wind turbine blade is statutory; and
    c. detecting defects in the composite on the surface of the wind turbine blade by identifying areas of the composite that are warmer or cooler than the surrounding background, where the inside region is cooled by blowing a fluid through an inside region of the wind turbine blade, and where the IR image obtained from said IR camera and any defects identified in said IR image can be located with respect to a physical location on the wind blade composite being inspected by identifying fiducials located on said wind blade in the IR image and based on the known pattern and location of these fiducials, transforming the coordinates of said IR image and said fiducials from the image to a coordinate system on said wind blade.

41. The method of claim 40, where said fiducials are electrical resistors.

42. The method of claim 40, where said fiducials are any material with different thermal properties than the composite.

43. The method of claim 40, where the fiducials are mounted in a felt mat.

44. The method of claim 43, where said fiducials and said felt mat are attached to a more rigid but flexible membrane such as a rubber material.

\* \* \* \* \*